US010660796B2

United States Patent
Wu

(10) Patent No.: US 10,660,796 B2
(45) Date of Patent: May 26, 2020

(54) WIRELESS PROJECTOR-TYPE WELDING HELMET AND WELDING MACHINE EQUIPPED WITH THE SAME

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 406 days.

(21) Appl. No.: 15/507,657

(22) PCT Filed: Sep. 1, 2015

(86) PCT No.: PCT/CN2015/088719
§ 371 (c)(1),
(2) Date: Feb. 28, 2017

(87) PCT Pub. No.: WO2016/145795
PCT Pub. Date: Sep. 22, 2016

(65) Prior Publication Data
US 2017/0290707 A1 Oct. 12, 2017

(30) Foreign Application Priority Data

Mar. 18, 2015 (CN) .......................... 2015 1 0119073

(51) Int. Cl.
*B23K 9/32* (2006.01)
*A61F 9/06* (2006.01)
(Continued)

(52) U.S. Cl.
CPC ................ *A61F 9/067* (2013.01); *A61F 9/06* (2013.01); *B23K 9/095* (2013.01); *B23K 9/32* (2013.01); *B23K 9/322* (2013.01); *F16P 1/06* (2013.01)

(58) Field of Classification Search
CPC .................. B23K 9/321–322; A61F 9/06–068
See application file for complete search history.

(56) References Cited

U.S. PATENT DOCUMENTS 5,959,705 A * 9/1999 Fergason ................. B23K 9/32
2/8.8
6,242,711 B1 6/2001 Cooper
(Continued)

FOREIGN PATENT DOCUMENTS

CN     101247917 A    8/2008
CN     104224438 A    12/2014
(Continued)

OTHER PUBLICATIONS

Miller Electric Manufacturing, Auto-Darkening Helmets, Sep. 2013 (Year: 2013).*
(Continued)

*Primary Examiner* — Michael A Laflame, Jr.

(57) ABSTRACT

The present application discloses a wireless projector-type auto-darkening welding helmet comprising: a helmet housing; a headband structure for securing the helmet housing; an auto-darkening filter secured on the helmet housing; a wireless communication module; and a micro-projector which is data-connected to the auto-darkening filter and the wireless communication module, wherein when the auto-darkening filter is in a transparent state, the micro-projector is adaptable to project operating parameters of the auto-darkening filter and/or data received by the wireless communication module, as images, onto a plane in front of the welding helmet such that they can be watched by an operator who wears the welding helmet on his/her head. The present application also discloses a welding apparatus equipped with said wireless projector-type auto-darkening welding helmet.

20 Claims, 7 Drawing Sheets

(51) Int. Cl.
*F16P 1/06* (2006.01)
*B23K 9/095* (2006.01)

(56) References Cited

U.S. PATENT DOCUMENTS

| | | | |
|---|---|---|---|
| 6,734,393 B1* | 5/2004 | Friedl | A61F 9/067 219/130.01 |
| 8,569,655 B2 | 10/2013 | Cole | |
| 9,895,267 B2 | 2/2018 | Cole | |
| 2007/0056073 A1* | 3/2007 | Martin | A61F 9/065 2/8.8 |
| 2010/0089887 A1 | 4/2010 | Friedl et al. | |
| 2011/0083241 A1* | 4/2011 | Cole | A61F 9/06 2/8.2 |
| 2011/0220616 A1* | 9/2011 | Mehn | B23K 9/291 219/74 |
| 2013/0242110 A1* | 9/2013 | Terre | H04N 5/2251 348/164 |
| 2014/0346158 A1 | 11/2014 | Matthews | |
| 2016/0022496 A1* | 1/2016 | DeKeuster | G02F 1/13306 349/14 |
| 2016/0209887 A1* | 7/2016 | Stewart | G06F 1/16 |
| 2016/0260261 A1* | 9/2016 | Hsu | G06T 19/006 |
| 2018/0301056 A1* | 10/2018 | Cross | G09B 19/003 |

FOREIGN PATENT DOCUMENTS

| | | |
|---|---|---|
| CN | 204050009 U | 12/2014 |
| JP | 2013-504437 A | 2/2013 |
| WO | 0158400 A1 | 8/2001 |
| WO | 2014039584 A1 | 3/2014 |

OTHER PUBLICATIONS

State Intellectual Property Office of the P.R. China, International Search Report in International Application No. PCT/CN2015/088719 (dated Dec. 25, 2015).

Extended European Search Report regarding Application No. 15885170.9, dated Oct. 29, 2018, 10 pages.

IP Australia Examination report No. 1 for standard patent application regarding Application No. 2015386867, dated May 17, 2019, 3 pages.

* cited by examiner

WIRELESS PROJECTOR-TYPE WELDING HELMET AND WELDING MACHINE EQUIPPED WITH THE SAME

CROSS-REFERENCE TO RELATED APPLICATIONS

This patent application is the U.S. national phase of International Patent Application No. PCT/CN2015/088719, filed Sep. 1, 2015, which claims the benefit of Chinese Patent Application No. 201510119073.7, filed on Mar. 18, 2015, which are incorporated by reference in their entireties herein.

FIELD

The present application generally relates to a wireless-type welding helmet provided with a micro-projector for displaying operation status data, and a welding machine equipped with said wireless-type welding helmet.

BACKGROUND

In recent years, an auto-darkening welding helmet has been widely used on welding sites. Such an auto-darkening welding helmet is generally equipped with an auto-darkening filter. The auto-darkening filter can work mainly because it is provided with a liquid crystal panel. The liquid crystal panel is transparent before welding-arc ignition. The liquid crystal panel becomes opaque at the moment of the welding-arc ignition starting, so as to protect an operator's eyes. The auto-darkening welding helmet is usually provided with an adjustment knob or button. Therefore, before wearing the welding helmet, the operator has to hold it in hand to set operating parameters, such as SENSITIVITY, delay time, shade, and weld mode or the like, of the auto-darkening filter. After the setting, the operator can wear the welding helmet to carry out a welding operation.

In case that the operating parameters must be adjusted repeatedly on welding sites (for example to alter the weld mode, SENSITIVITY or the like), repeatedly taking off/wearing the helmet will extremely consume the operator's energy, which may negatively affect the quality of welding. Further, during taking off the helmet again, the operator's eyes have to be continuously self-adjustable to adapt to bright or dark ambient environmental change. Individual operators may even feel discomfort such that their welding work may be affected. In more serious cases their eyes may be permanently damaged.

Take an argon arc welding machine for example. A modern welding apparatus generally comprises an electric welding machine, a gas cylinder, a welding torch and a welding helmet. Before the welding operation is carried out, it is required to correspondingly set parameters of the electric welding machine, such as its electric current, voltage, welding duration time, wire feed speed or the like. The electric welding machine is provided with a display screen on its operating panel to show the parameters and their setting. A cable is connected between the electric welding machine and the welding helmet such that after the relevant operating parameters of the electric welding and the welding helmet have been properly set, the operator can wear the helmet to begin to work.

There is a possibility that the operator is stumbled by the connecting cable between the electric welding machine and the welding helmet. Further, due to its length limitation, the cable may constrain the operator's welding work in a specific circumstance. Furthermore, since the welding environment is usually severe, the connecting cable may become aged after it is used for a long period or may be broken off due to snarling, which may lead to signal connection interruption such that the welding helmet cannot be used normally.

SUMMARY

It is an object of the present application to provide an improved auto-darkening welding helmet such that the operator can set operating parameters of the welding helmet's auto-darkening filter without repeatedly taking off and wearing the helmet. Further, the operator can always wear said provided welding helmet and at the same time set the various operating parameters so as to facilitate his/her welding work.

According to one aspect of the present application, a wireless projector-type auto-darkening welding helmet is provided, which comprises:
   a helmet housing;
   a headband structure for securing the helmet housing;
   an auto-darkening filter secured on the helmet housing;
   a wireless communication module; and
   a micro-projector which is data-connected to the auto-darkening filter and the wireless communication module,
   wherein when the auto-darkening filter is in a transparent state, the micro-projector is adaptable to project operating parameters of the auto-darkening filter and/or data received by the wireless communication module, as images, onto a plane in front of the welding helmet such that they can be watched by an operator who wears the welding helmet on his/her head.

In one preferred embodiment, the micro-projector is integrated within the helmet housing or is detachably installed on the helmet housing.

In one preferred embodiment, an adjustment knob is installed on the helmet housing of the welding helmet and is used to adjust the operating parameters of the auto-darkening filter via a control circuit of the welding helmet.

In one preferred embodiment, adjustment of the operating parameters of the auto-darkening filter comprises adjustment of SHADE, which can be adjusted between 5 and 8 levels/9 and 13 levels; adjustment of SENSITIVITY, which can be adjusted between 0 and 10 levels; adjustment of DELAY TIME, which can be adjusted between 0 and 10 levels; and adjustment of welding mode, which can be switched between WELD, GRIND and CUTTING.

In one preferred embodiment, said wireless communication module is wirelessly connected to a wireless communication module of an electric welding machine, and the received data comprise operating parameters of the electric welding machine and/or a welding torch's operating time.

In one preferred embodiment, the wireless communication module comprises a WIFI module, a blue tooth module or an infrared data module.

In one preferred embodiment, the micro-projector's focal distance can be manually or automatically adjusted such that an image can be clearly projected onto a plane at a distance of 1~3 m in front of the helmet housing.

In one preferred embodiment, the knob is used to adjust the operating parameters of the electric welding machine and/or the welding torch's operating time, and adjustment of the operating parameters of the electric welding machine comprises current magnitude adjustment, voltage magnitude adjustment and/or AC-DC switching.

In one preferred embodiment, the micro-projector's focal distance can be manually or automatically adjusted, and the micro-projector can be used to project a black-and-white or colorful image.

In one preferred embodiment, the auto-darkening filter is provided with an independent liquid crystal display screen which is used to reveal the operating parameters of the auto-darkening filter and/or the data received by the wireless communication module of the welding helmet independently of projection by the micro-projector.

According to another aspect of the present application, a welding apparatus is provided, which comprises:

an electric welding machine equipped with a wireless communication module;

a torch connected to the electric welding machine via a cable;

a gas cylinder connected to the electric welding machine via a pipeline; and the wireless projector-type auto-darkening welding helmet as cited previously, wherein a wireless communication module of the wireless projector-type auto-darkening welding helmet is wirelessly connected to the wireless communication module of the electric welding machine.

With the welding helmet according to the present application, it is unnecessary for the operator to set the operating parameters of the auto-darkening filter by repeatedly taking off/wearing the helmet. The discomfort felt by the operator due to continuous self-adjustment to bright or dark ambient environment can be reduced. In the meanwhile, the operating parameters can be adjusted by the operator who can always wear the helmet and thus the operator's welding work is facilitated. Further, the improved auto-darkening welding helmet is also equipped with the wireless communication module for receiving and showing the operating parameters of the welding apparatus's electric welding machine, such that the operating parameters of the electric welding machine can be directly watched by the operator wearing the helmet. This facilitates observation of the operator and reduces the probability that the operator may be damaged in a welding operation. Moreover, the operating parameters of the electric welding machine can be intuitively revealed onto the welding helmet without any limitation due to the cable length so as to facilitate the operator real-timely observing and/or adjusting the electric welding machine's state. Since the operator, who is wearing the helmet, can adjust the operating parameters, his/her work convenience is improved while he/she will not feel any discomfort caused by the eyes continuous self-adjustment to rapid bright or dark environmental light change. Therefore, the operator's work efficiency will be enhanced.

Further, with the inventive welding helmet, the operator can real-timely observe the operating parameters of the electric welding machine or adjust the relevant parameters via the adjustment knob on the helmet without taking off the helmet. This facilitates the operator working on welding sites. In the meanwhile, the cable constrain is eliminated and the possibility that the operator may be damaged can be avoided.

BRIEF DESCRIPTION OF THE DRAWINGS

The foregoing and other aspects of the present application will be well understood by the following description in combination of the attached drawings. It should be noted that the drawings are illustrated in different scales for clarity, which however does not influence understanding to the present application. In the drawings.

DETAILED DESCRIPTION

Figure 1:
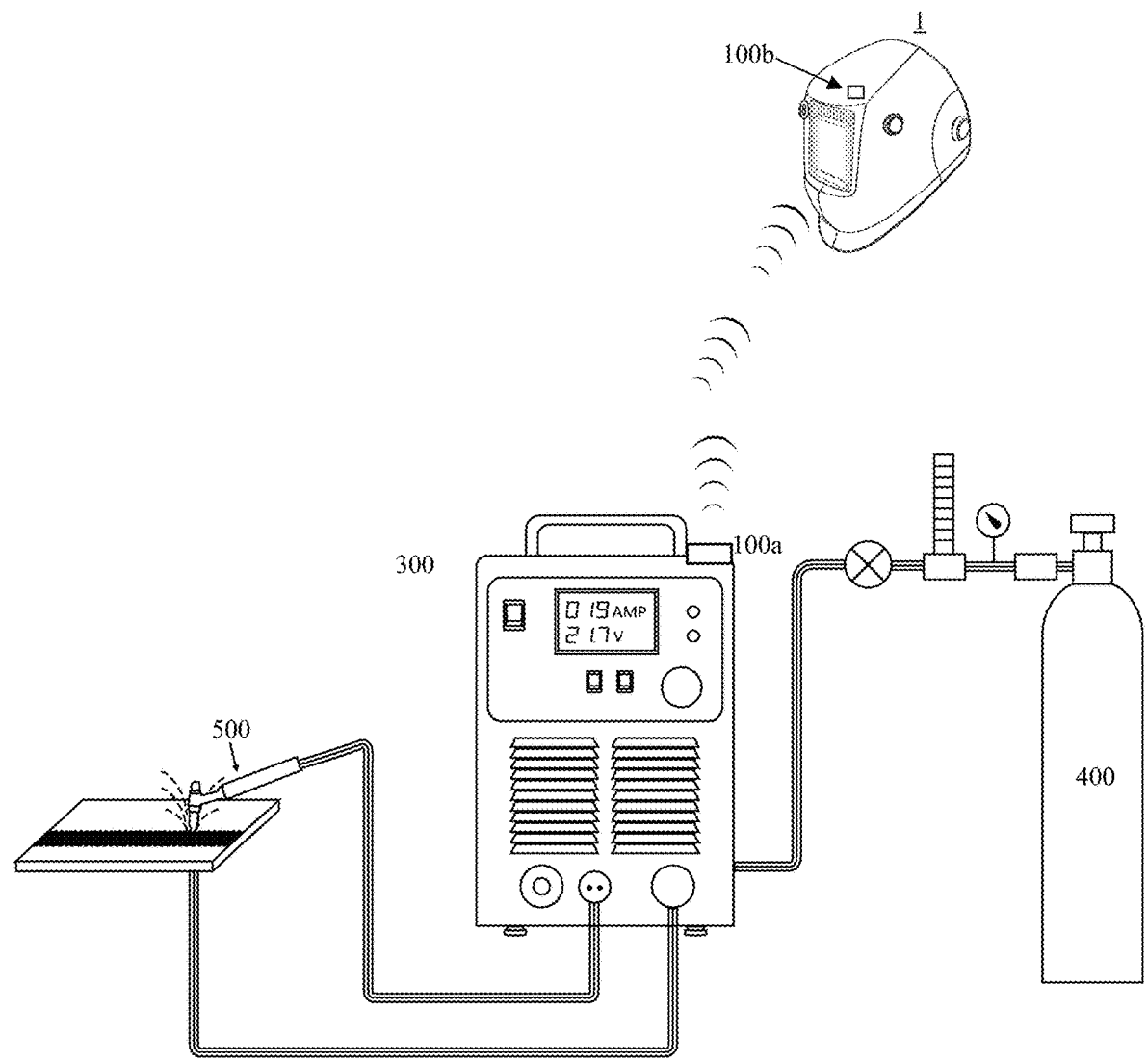
FIG. 1 schematically illustrates a welding apparatus according to an embodiment of the present application.

In the drawings of the present application, the same or similar features are represented by the same reference numerals.

Figure 4:
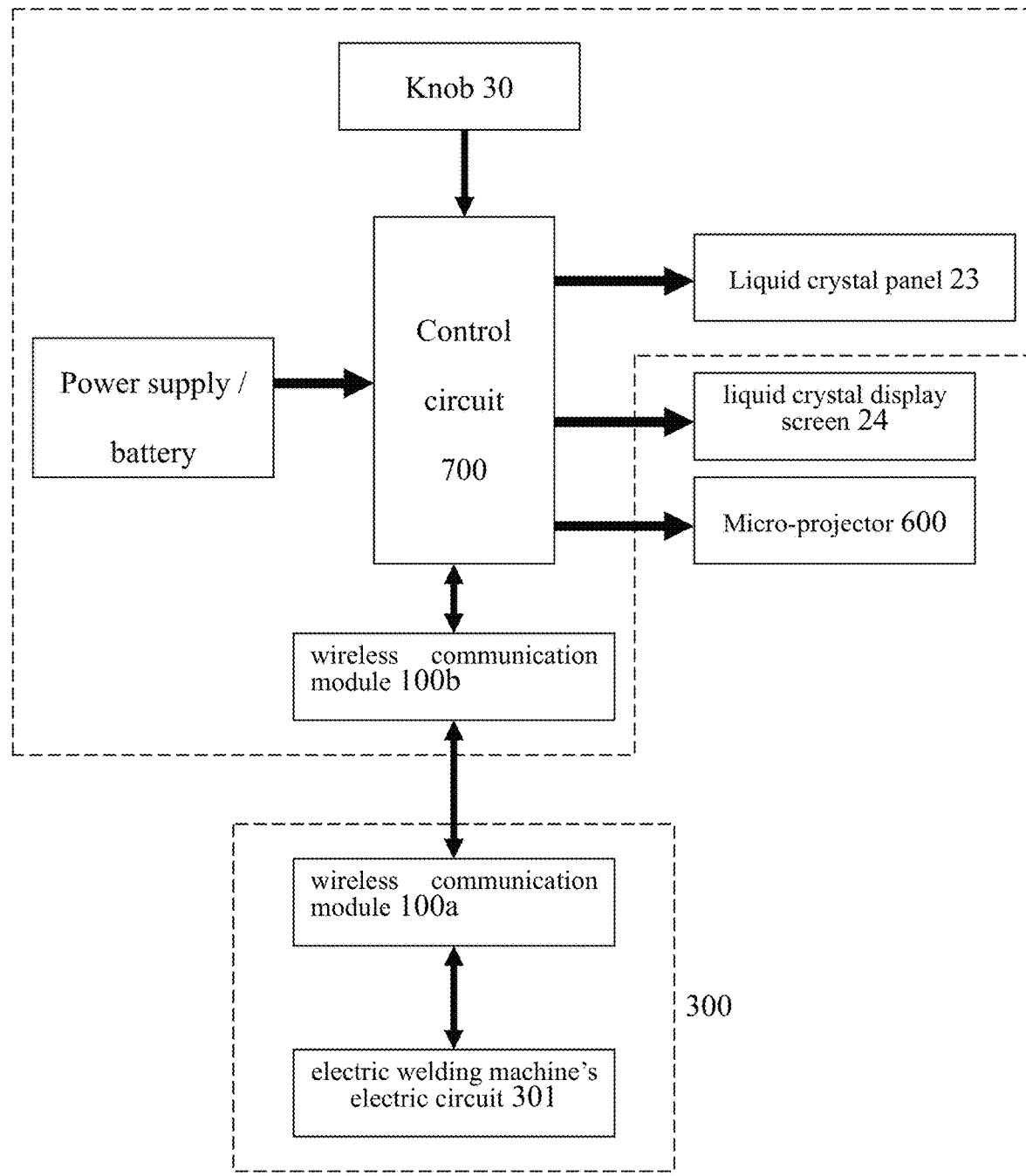
FIG. 4 is a simplified control block diagram schematically illustrating the welding apparatus according to the present application.

FIG. 1 schematically illustrates a welding apparatus according to an embodiment of the present application. The welding apparatus comprises an electric welding machine 100, a gas cylinder 400 (for example an argon gas cylinder), and a welding torch 500. The electric welding machine 100, the gas cylinder 400 and the welding torch 500 are connected to each other via cables in a manner known in the art. Additionally, the welding apparatus comprises a wireless communication module 100a provided on the electric welding machine 300. The wireless communication 100a is connected to an electric circuit 301 of the electric welding machine (as shown in FIG. 4) and can be used to send relevant signals indicative of operating parameters of the electric welding machine such as current magnitude, voltage magnitude, AC or DC exhibition, and the torch's operating time or the like. After the module receives control instructions, the electric circuit of the electric welding machine can be adjusted so as to vary the operating parameters of the electric welding machine correspondingly.

It is appreciated that the wireless communication module 100a is not limited to be located at a position on the electric welding machine 300 as shown in FIG. 1; alternatively it can be provided within a housing of the electric welding machine 300 such that it can be hidden therein.

Figure 2:
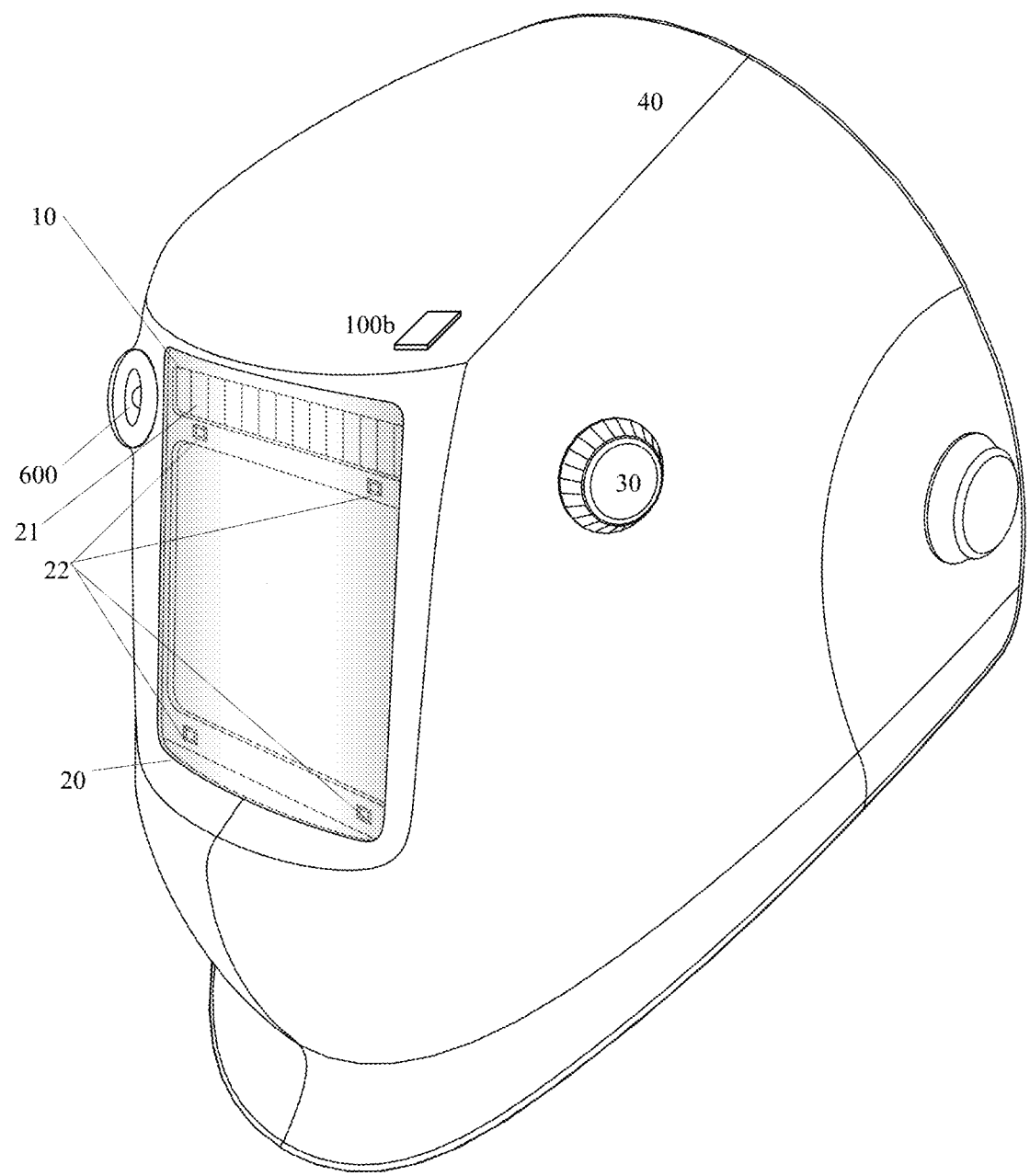
FIG. 2 schematically illustrates a perspective view of a wireless projector-type welding helmet according to an embodiment of the present application.

FIG. 2 is a perspective view schematically illustrating a wireless projector-type welding helmet 1 according to an embodiment of the present application. The welding helmet 1 comprises a helmet housing 40, a HUD (Head-Up Display)-type auto-darkening filter 10 installed at the front of the helmet housing 40, and a headband structure 60 (see FIG. 5). The headband structure 60 is coupled to an inner side of the helmet housing 40 and is used to be worn directly on an operator's head to secure the helmet housing 40 there in place.

The auto-darkening filter 10 has a body on which a solar battery module 21, a photosensitive module 22, and a liquid crystal panel 23 are integrated. The liquid crystal panel is transparent before welding-arc ignition. The liquid crystal panel becomes opaque at the moment of the welding-arc ignition, so as to protect the operator's eyes.

A protective sheet 20 is disposed in front of the auto-darkening filter 10. The protective sheet 20 is transparent so as to protect the auto-darkening filter 10 from spattering matters caused by a welding operation.

A control knob 30 is provided on the helmet housing 40. The control knob 30 is connected to the auto-darkening filter 10 via a data cable not shown in this view, and is used to adjust the auto-darkening filter's operating parameters. Here, the adjustable operating parameters of the auto-darkening filter 10 comprise SHADE, which can be adjusted between 5 and 8 levels/9 and 13 levels; SENSITIVITY, which can be adjusted between 0 and 10 levels; DELAY TIME, which can be can be adjusted between 0 and 10 levels; and welding modes such as WELD, GRIND and CUTTING.

As shown in FIG. 2, the welding helmet 1 is also provided with a wireless communication module 100*b* thereon. For example, this wireless communication module 100*b* can be provided on the helmet housing 40 above the protective sheet 20. It is appreciated by a person skilled in the art that the wireless communication module 100*b* can be alternatively provided at any position of the helmet housing 40 where signal sending/receiving cannot be affected, for example is hiddenly provided within the helmet housing 40.

The wireless communication module 100*b* can be connected to a control circuit of the welding helmet as shown in FIG. 4 such that under the control of the knob 30 the module can send instructions for controlling the electric welding machine 300 outwards via the wireless communication module 100*b* or can process data information received from the wireless communication module 100*a*. The wireless communication modules 100*a* and 100*b* each can be a Wireless Fidelity based module (WIFI modules), a blue tooth module, an infrared data module or any other suitable communication module which can carry out wireless data connection.

According to the present application, as shown in FIG. 2, the welding helmet 1 further comprises a micro-projector 600. In the embodiment illustrated by FIG. 2, the micro-projector 600 is inbuilt within the helmet housing 40 of the welding helmet 1.

For instance, the micro-projector in the present application can be a projector device based on micro laser projection technology. For instance, the projector device can be DMD (Digital Micromirror Device) available from Texas Instruments Inc. (T.I.), LCos (Liquid Crystal on Silicon) available from 3M, LCD (Liquid Crystal Display) available from Explay Inc. or other suitable and relevant products. In an alternative embodiment, any other micro projector device based on MEMS and projection technologies and available on the market can be used in the present application as the projector device.

The micro-projector 600 is located aside the auto-darkening filter 10 and is connected to the auto-darkening filter 10 via a relevant cable. The micro-projector is configured such that it can be controlled by the control knob 30 via the control circuit 700 of the welding helmet 1 (as shown in FIG. 4).

Figure 3:
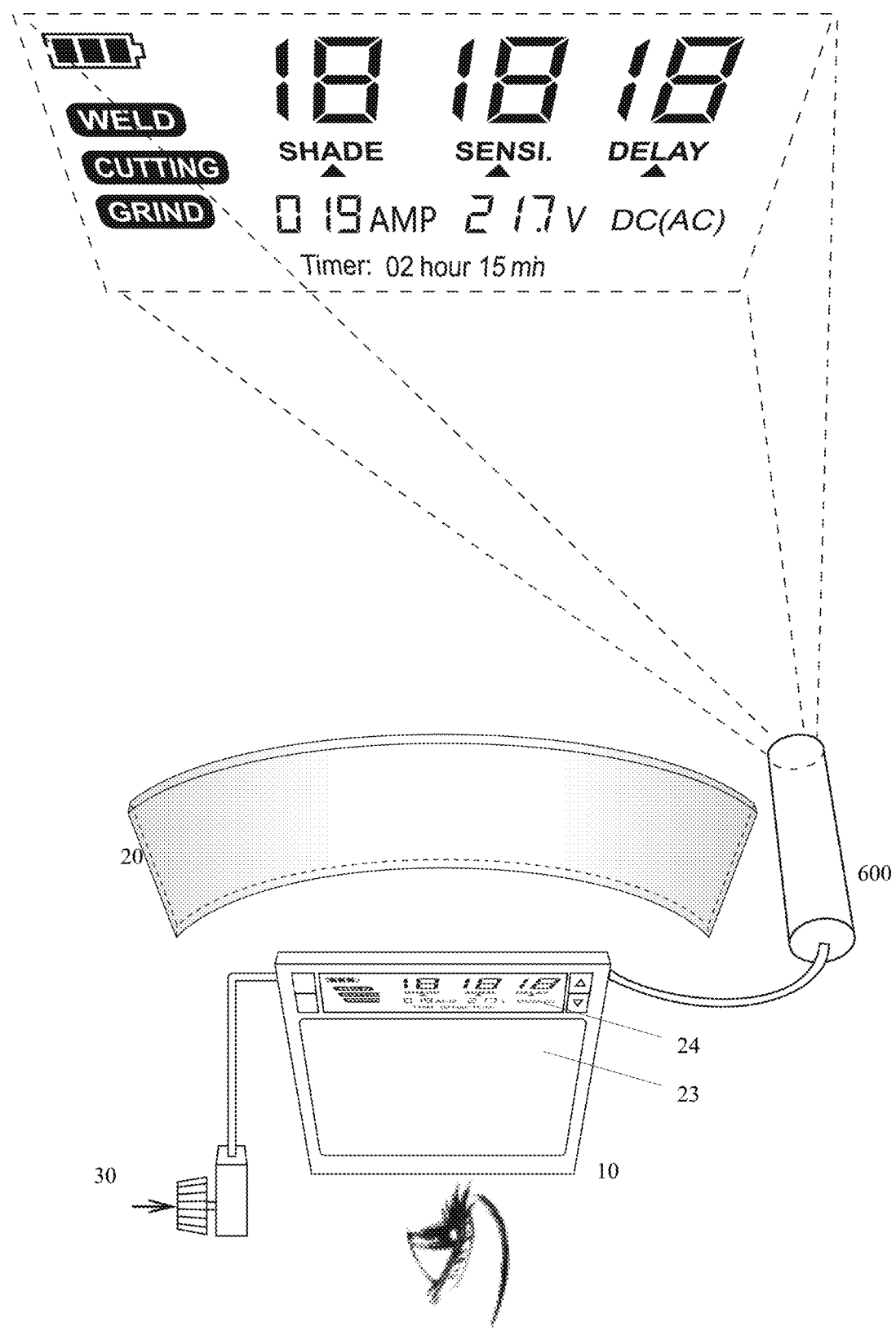
FIG. 3 schematically illustrates the configuration of an auto-darkening filter which is equipped with a micro-projector and used in the welding helmet according to the present application.

As shown in FIGS. 1 and 3, the micro-projector 600 can be designed such that when the auto-darkening filter 10 is in a transparent state, the micro-projector can project adjustments of SHADE, which can be adjusted between 5 and 8 levels/9 and 13 levels; of SENSITIVITY, which can be adjusted between 0 and 10 levels; of DELAY TIME, which can be can be adjusted between 0 and 10 levels; and of welding modes such as WELD, GRIND and CUTTING, onto a frontal plane as images. As shown in FIG. 3, an independent liquid crystal display screen 24 is provided on the auto-darkening filter 10 to reveal the above-mentioned operating parameters of the auto-darkening filter 10. In one preferred embodiment, said liquid crystal display screen 24 is located on a side of the auto-darkening filter 10 facing towards the operator's face after he/she has worn the welding helmet 1. For instance, before the operator first wears the welding helmet 1 on his/her head, the relevant operating parameters of the auto-darkening filter 10 can be revealed by the independent liquid crystal display screen 24 in advance and thus can be adjusted by the knob 30. Thereafter, the operator can wear the welding helmet 1 on his/her head.

For instance, during the welding operation, the operator, who wears the welding helmet 1 on his/her head, can slightly lower his/her head such that the operating parameters can be projected, as images, onto the ground. In this way, the operating parameters can be directly watched by the operator, who does not take off the welding helmet 1 from his/her head, and can be reset by the control knob 30.

For instance again, during the welding operation, on welding sites, the operator, who wears the welding helmet 1 on his/her head, can project the images of the operating parameters onto a vertical face beside him/her, for example a wall face, such that the operating parameters can be directly watched by the operator and can be reset by means of the control knob 30.

FIG. 4 is a simplified control block diagram schematically illustrating the welding apparatus according to the present application. A battery is connected to the liquid crystal panel 23 and the liquid crystal display screen 24 via the control circuit 700 of the welding helmet 1, and the knob 30 is also connected to the liquid crystal panel 23 and the liquid crystal display screen 24 via the control circuit 700 such that the operating parameters of the auto-darkening filter 10 can be adjusted by the knob 30. Furthermore, the control circuit 700 is connected to the wireless communication module 100*b* such that by data exchange between the wireless communication modules 100*a* and 100*b*, the operating parameters of the electric welding machine 300 can be real-timely projected by the micro-projector 600 outwards as images. In this way, the operating parameters, such as current magnitude, voltage magnitude, AC or DC exhibition, welding torch operating time or the like, of the electric welding machine 300 can be imaged in a way similarly shown in FIG. 2.

As shown in FIG. 3, the independent display screen of the auto-darkening filter 10 can be also used to independently reveal the operating parameters of the electric welding machine 300. For instance, before the operator first wears the welding helmet 1 on his/her head, the operating parameters of the electric welding machine 300 can be revealed by the independent liquid crystal display screen 24 in advance and thus can be adjusted by the knob 30. Thereafter, the operator can wear the welding helmet 1 on his/her head.

For example, during the welding operation, after the welding helmet 1 has been worn by the operator, the operating parameters of both of the auto-darkening filter 10 and the electric welding machine 300 can be projected, via the micro-projector 600 and by means of the wireless communication modules 100*a* and 100*b*, onto a plane near the operator as images, which can be readily watched by the operator. Then, after the operator presses the knob 30 and rotates it, a virtual image corresponding to one operating parameter such as current is highlighted. Subsequently, pressing the knob 30 again and rotating it can enable the current magnitude to be increased or decreased correspondingly. After the current magnitude is suitably chosen, the adjustment can be finished by pressing the knob 30 again. How to operate and adjust the operating parameters by the knob 30 has been explained above as an illustrative example only. It is appreciated by the skilled person in the art that on the basis of the same principle the knob 30 can be redesigned to work in other suitable manners.

The micro-projector 600 has a focal distance which is for example about 1 m (meter), preferably between 1 m and 3 m. In this way, when the operating parameter images are projected onto a plane ahead of the operator's head by 1 m, the operator can watch the images most clearly. In an alternative embodiment, the micro-projector can be provided with a manual focusing mechanism by which the operator can manually adjust the focal distance conveniently such that a clearer image can be generated at a plane of a suitable distance. It is appreciated that the micro-projector in the present application can be a projector for projecting black-and-white or colorful images. In one preferred embodiment, the brightness of the micro-projector can be manually or automatically adjusted.

Figure 5:
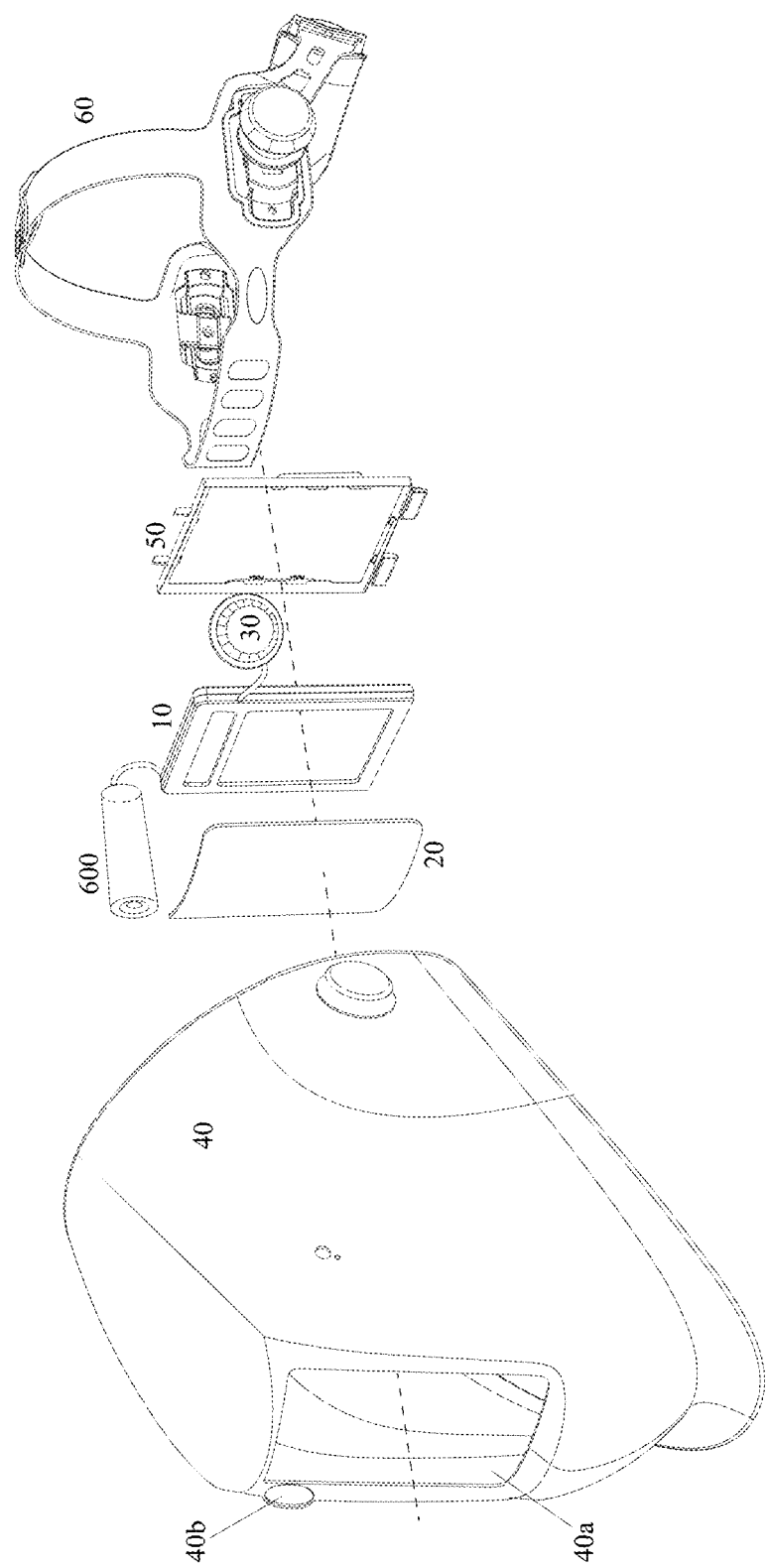
FIG. 5 is an exploded and perspective view schematically illustrating the wireless projector-type welding helmet shown in FIG. 2.
Figure 6:
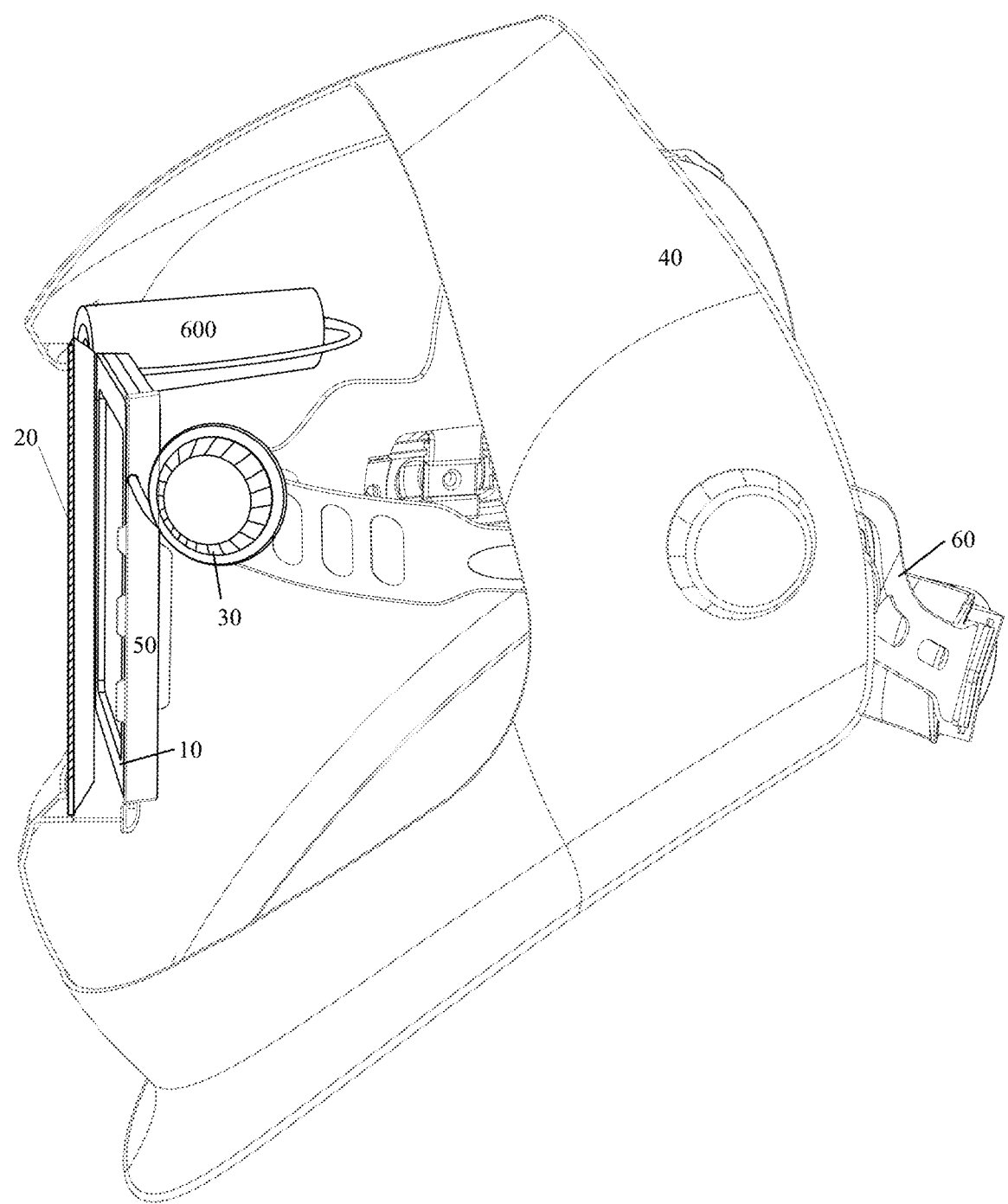
FIG. 6 is a partially cut and perspective view schematically illustrating the wireless projector-type welding helmet shown in FIG. 2.

The welding helmet 1 according to the embodiment of the present application will be further explained with respect to FIGS. 5 and 6. The headband structure 60 is used to be directly worn on the operator's head, so as to secure the helmet housing 40 there in place. A substantially rectangular opening 40a is provided in a front part of the helmet housing 40. For example, a support frame 50 is detachably installed in the opening 40a. The auto-darkening filter 10 is securely installed in the support frame 50. It should be understood that the auto-darkening filter 10 can be secured into the support frame 50 via any suitable manner such as bonding, screw fastening, crimping, snapping or the like, known by the skilled person in the art.

The knob 30 for adjusting the auto-darkening filter 10 is provided on the helmet housing 40 such that the operator wearing the helmet 1 can manipulate the knob 30 with his/her hand to adjust the operating parameters. The transparent protective sheet 20 is arranged at the opening 40a of the helmet housing 40 in front of the auto-darkening filter 10. It should be understood that the protective sheet 20 can be secured between the support frame 50 and the helmet housing 40 in the opening 40a of the helmet housing 40 via any suitable manner such as bonding, screw fastening, crimping, snapping or the like.

Additionally, the helmet housing 40 is provided with an opening 40b which is located aside the opening 40a. The micro-projector 600 can be inserted into the opening 40b such that image can be projected outwards by light from the micro-projector through the opening 40b. The micro-projector 600 can be fixed at a position on the helmet housing 400 where the headband structure 60 is not affected. In the embodiment shown by FIGS. 5 and 6, the micro-projector 600 is inbuilt and integrated in the welding helmet.

Figure 7:
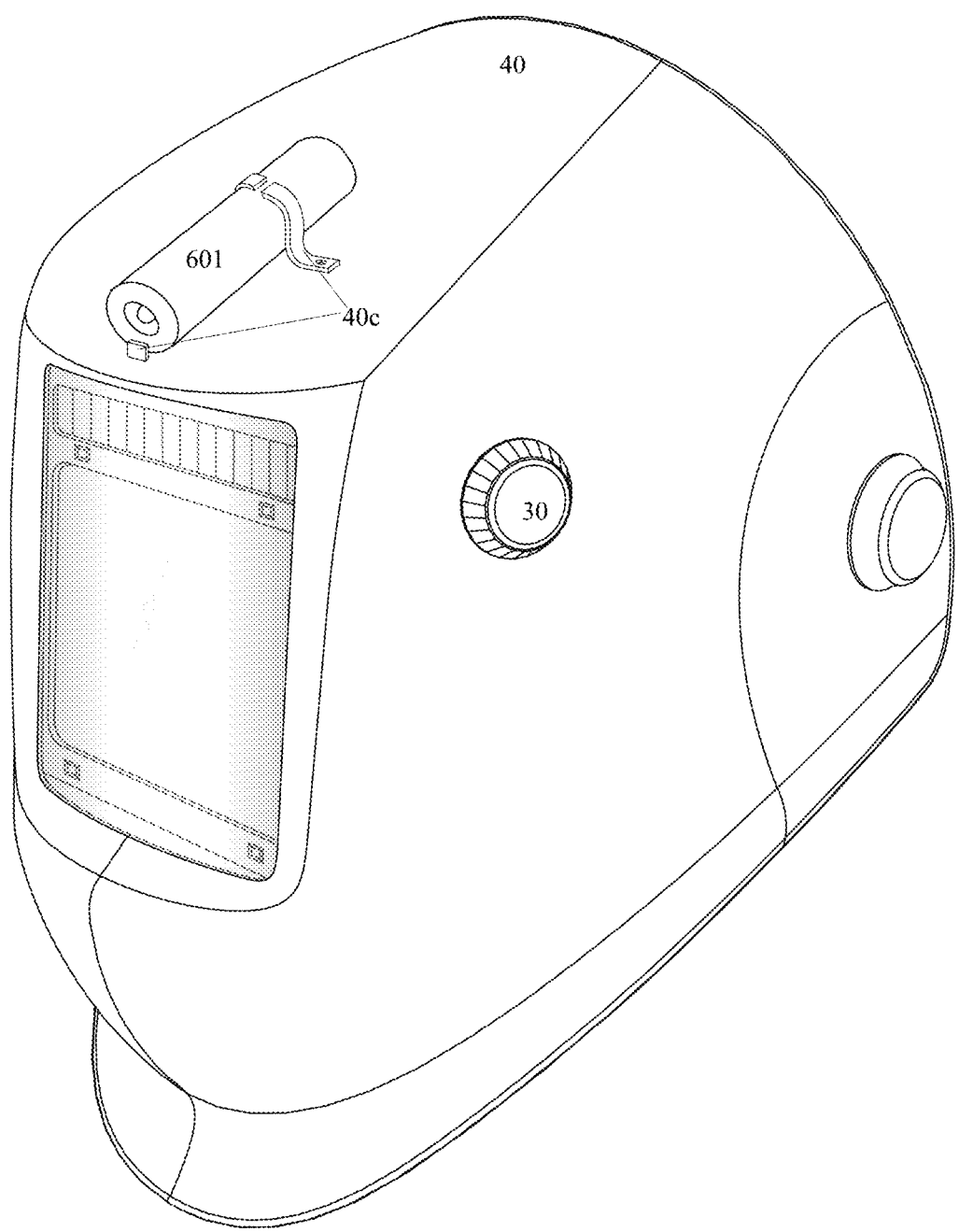
FIG. 7 is a perspective view schematically illustrating a wireless projector-type welding helmet according to another embodiment of the present application.

FIG. 7 schematically illustrates a welding helmet according to another embodiment of the present application. This welding helmet is distinguished from that illustrated by FIGS. 5 and 6 only in that the former welding helmet is provided with an external micro-projector 601. The micro-projector 601 is detachably installed on the top of the helmet housing 40 via a suitable fixation device 40c, for example a clip. Power and data cables for the micro-projector 601 can be provided on the helmet housing 1 respectively. The external micro-projector is advantageous in that in case of failure it can be readily replaced by a new one or that a manual focusing mechanism can be directly provided on the micro-projector 601 to adjust its focal distance or the orientation of the micro-projector 601 can be readily adjusted even if the operator's head is not moved, such that the operator can find a suitable projecting plane where images can be projected. It should be understood that the external micro-projector 601 can be provided on the helmet housing 40 at any position where the auto-darkening filter's normal work is not affected.

It is appreciated that the micro-projector 600 or 601 according to the present application can be designed such that image projection can be carried out only when the auto-darkening filter 10 is in the transparent state.

Alternatively, as shown in FIG. 3, an adjustment key can be provided at either side of the independent liquid crystal display screen 24, which key can be used to cooperate with the knob 30 to adjust the operating parameters of the auto-darkening filter 10 and/or the electric welding machine 300 before the operator first wears the welding helmet 1 on his/her head.

On the contrary to conventional welding helmets, the wireless projector-type welding helmet can be directly worn by the operator such that when the auto-darkening filter 10 becomes transparent the operating parameters of the auto-darkening filter and/or the electric welding machine can be projected by the micro-projector, as images, onto a plane at a suitable distance from his/her body. Those parameters can be manually adjusted. Then, a welding operation with welding-arc ignition starting can be carried out directly after the micro-projector is powered off. Further, during the welding operation, in order to alter the operating parameters or the welding mode, the micro-projector can be powered on again after the auto-darkening filter 10 is enabled to be transparent. In this case, the respective operating parameters can be altered. Then, the welding operation can be continued. It can be seen that using the wireless projector-type welding helmet according to the present application, the operator can directly adjust the respective operating parameters with wearing the helmet on his/her head such that it is not necessary for him/her to take off the helmet, adjust the operating parameters, and wear the helmet on his/her head again as required by the prior art. The operator's work convenience is improved and at the same time his/her eyes will not feel any discomfort caused by rapid bright or dark environmental light change. Therefore, the operator's work efficiency is improved. Moreover, using the inventive welding helmet, the operator can carry out the welding operation especially in a dark environment because the image generated by the micro-projector will be much clearer in this case.

Furthermore, with the welding helmet equipped with the wireless communication module according to the present application, the operator will not be constrained by a cable connected between the welding helmet and the electric welding machine as required by the prior art. Any possible limitation on welding sites is avoided. The operating parameters of the electric welding machine can be real-timely watched and adjusted by the operator. In this way, the operating parameters of the electric welding machine are adjustable depending on welding requirements, whenever necessary, such that the operator's work efficiency can be improved.

Although the specific embodiments of the present application have been explained in details, they are given for illustrative purposes only and cannot be though to constitute any limitation to the present application. Any modification, change or combination to the embodiments described here which can be made by those skilled in the art after reading the present specification without departing from the spirit of the present application fall within the scope of the present application.

The invention claimed is:

1. A wireless projector-type auto-darkening welding helmet, comprising:
   a helmet housing comprising a knob installed on an exterior of the helmet housing;
   a headband structure for securing the helmet housing;
   an auto-darkening filter secured on the helmet housing;
   a wireless communication module configured to receive data from an electric welding machine, wherein, based on a movement of the knob, the wireless communication module is configured to transmit instructions to adjust operating parameters of the electric welding machine; and
   a micro-projector which is data-connected to the auto-darkening filter and the wireless communication module,
   wherein when the auto-darkening filter is in a transparent state, the micro-projector is adaptable to project at least one of operating parameters of the auto-darkening filter or data received by the wireless communication module as images onto a plane in front of the welding helmet such that the images can be watched by an operator who wears the welding helmet on his or her head.

2. The welding helmet as recited in claim 1, wherein the micro-projector is integrated within the helmet housing or is detachably installed on the helmet housing.

3. The welding helmet as recited in claim 1, wherein the knob is further configured to adjust the operating parameters of the auto-darkening filter via a control circuit of the welding helmet.

4. The welding helmet as recited in claim 1, wherein adjustment of the operating parameters of the auto-darkening filter comprises adjustment of SHADE, which can be adjusted between 5 and 8 levels/9 and 13 levels; adjustment of SENSITIVITY, which can be adjusted between 0 and 10 levels; adjustment of DELAY TIME, which can be adjusted between 0 and 10 levels; and adjustment of welding mode, which can be switched between WELD, GRIND and CUTTING.

5. The welding helmet as recited in claim 1, wherein:
   the wireless communication module is wirelessly connected to a second wireless communication module corresponding to the electric welding machine; and
   the received data comprises at least one of operating parameters of the electric welding machine or an operating time of a welding torch.

6. The welding helmet as recited in claim 1, wherein the wireless communication module comprises a WiFi module, a Bluetooth module, or an infrared data module.

7. The welding helmet as recited in claim 1, wherein a focal distance of the micro-projector can be manually or automatically adjusted such that the image can be clearly projected onto a plane at a distance of 1~3 m in front of the helmet housing.

8. The welding helmet as recited in claim 1, wherein:
   the knob is further configured to adjust an operating time of a welding torch, and
   the adjustment of the operating parameters of the electric welding machine comprises at least one of current magnitude adjustment, voltage magnitude adjustment, or AC-DC switching, and
   the movement of the knob to adjust the operating parameters of the electric welding machine comprises a press toward the helmet housing and a rotation.

9. The welding helmet as recited in claim 1, wherein:
   a focal distance of the micro-projector can be manually or automatically adjusted; and
   the micro-projector is configured to project a black-and-white or colorful image.

10. The welding helmet as recited in claim 1, wherein the auto-darkening filter includes an independent liquid crystal display screen configured to display at least one of the operating parameters of the auto-darkening filter or the data received by the wireless communication module of the welding helmet independently of projection by the micro-projector.

11. A welding system, comprising:
    an electric welding machine equipped with a first wireless communication module;
    a torch connected to the electric welding machine via a cable;
    a gas cylinder connected to the electric welding machine via a pipeline; and
    a wireless projector-type auto-darkening welding helmet, including:
       a helmet housing comprising a knob installed on an exterior of the helmet housing,
       a headband structure for securing the helmet housing,
       an auto-darkening filter secured on the helmet housing,
       a second wireless communication module wirelessly connected to the first wireless communication module and configured to receive data from the first wireless communication module, wherein, based on a movement of the knob, the second wireless communication module is configured to transmit instructions to the first wireless communication module to adjust operating parameters of the electric welding machine, and
       a micro-projector which is data-connected to the auto-darkening filter and the second wireless communication module,
    wherein when the auto-darkening filter is in a transparent state, the micro-projector is adaptable to project at least one of operating parameters of the auto-darkening filter or data received by the wireless communication module as images onto a plane in front of the welding helmet such that the images can be watched by an operator who wears the welding helmet on his or her head.

12. The welding system of claim 11, wherein the micro-projector is integrated within the helmet housing or is detachably installed on the helmet housing.

13. The welding system of claim 11, wherein the knob is further configured to adjust the operating parameters of the auto-darkening filter via a control circuit of the welding helmet.

14. The welding system of claim 11, wherein adjustment of the operating parameters of the auto-darkening filter comprises adjustment of SHADE, which can be adjusted between 5 and 8 levels/9 and 13 levels; adjustment of SENSITIVITY, which can be adjusted between 0 and 10 levels; adjustment of DELAY TIME, which can be adjusted between 0 and 10 levels; and adjustment of welding mode, which can be switched between WELD, GRIND and CUTTING.

15. The welding system of claim 11, wherein the received data comprises at least one of operating parameters of the electric welding machine or an operating time of the torch.

16. The welding system of claim 11, wherein the second wireless communication module comprises a WiFi module, a Bluetooth module, or an infrared data module.

17. The welding system of claim 11, wherein a focal distance of the micro-projector can be manually or automatically adjusted such that the image can be clearly projected onto a plane at a distance of 1~3 m in front of the helmet housing.

18. The welding system of claim 11, wherein:
the knob is further configured to adjust an operating time of the torch,
the adjustment of the operating parameters of the electric welding machine comprises at least one of current magnitude adjustment, voltage magnitude adjustment, or AC-DC switching, and
the movement of the knob to adjust the operating parameters of the electric welding machine comprises a press toward the helmet housing and a rotation.

19. The welding system of claim 11, wherein:
a focal distance of the micro-projector can be manually or automatically adjusted; and
the micro-projector is configured to project a black-and-white or colorful image.

20. The welding system of claim 11, wherein the auto-darkening filter includes an independent liquid crystal display screen configured to display at least one of the operating parameters of the auto-darkening filter or the data received by the wireless communication module of the wireless projector-type auto-darkening welding helmet independently of projection by the micro-projector.

* * * * *